United States Patent [19]

Gonze

[11] Patent Number: 4,971,015

[45] Date of Patent: Nov. 20, 1990

[54] COMBUSTION ENGINE WITH MULTI-FUEL CAPABILITY

[75] Inventor: Eugene V. Gonze, Sterling Heights, Mich.

[73] Assignee: General Motors Corporation, Detroit, Mich.

[21] Appl. No.: 499,148

[22] Filed: Mar. 26, 1990

Related U.S. Application Data

[62] Division of Ser. No. 268,431, Nov. 8, 1988, Pat. No. 4,915,084.

[51] Int. Cl.[5] ............................................. F02M 51/00
[52] U.S. Cl. .................................. 123/494; 123/478; 73/61 R
[58] Field of Search ............... 123/478, 494, 575, 1 A; 324/58.5 A; 73/61 R

[56] References Cited

U.S. PATENT DOCUMENTS

| | | | |
|---|---|---|---|
| 3,816,811 | 6/1974 | Cmelik | 324/61 R |
| 4,001,676 | 1/1977 | Hile et al. | 73/304 C |
| 4,323,046 | 4/1982 | Barber | 123/575 |
| 4,438,749 | 3/1984 | Schwippert | 123/494 |
| 4,453,125 | 6/1984 | Kimura et al. | 324/58.5 A |
| 4,470,300 | 9/1984 | Kobayashi | 73/304 C |
| 4,706,630 | 11/1987 | Wineland et al. | 123/575 |

FOREIGN PATENT DOCUMENTS

1232675  5/1971  United Kingdom .

OTHER PUBLICATIONS

"Vehicle Operation with Variable Methanol/Gasoline Mixtures", *VI International Symposium on Alcohol Fuels Technology*, May 1984.
"An On-Board Sensor for Percent Alcohol", *IEEE Transactions on Vehicular Technology*, vol. VT-27, No. 3, Aug. 1978.

*Primary Examiner*—E. Rollins Cross
*Attorney, Agent, or Firm*—Robert M. Sigler

[57] ABSTRACT

A combustion engine has apparatus effective to provide a fuel mixture of one or more liquid fuels such as gasoline of variable aromatic content, normal alcohols, co-solvents, octane improvers and hydrocarbons having different energy contents in an unknown combination and combine it with air in a controlled A/F ratio with an input from a fuel mixture dielectric constant sensor. The sensor comprises a capacitor in the fuel line near the engine so that the dielectric constant of the fuel mixture about to enter the engine determines the capacitance, a resistor in series with the capacitor, an oscillator providing an oscillating voltage across the resistor and capacitor at a high frequency of at least 1 MHz but less than a frequency requiring microwave components, and an electric circuit responsive to a capacitively determined electrical parameter of the capacitor such as the voltage thereacross to determine the capacitance thereof and therefore the dielectric constant of the fuel mixture. The high frequency of the circuit avoids problems of high conductivity in fuel mixtures having high alcohol concentrations which would short out the capacitor at lower frequencies and offers additional advantages over optical and microwave sensors.

4 Claims, 2 Drawing Sheets

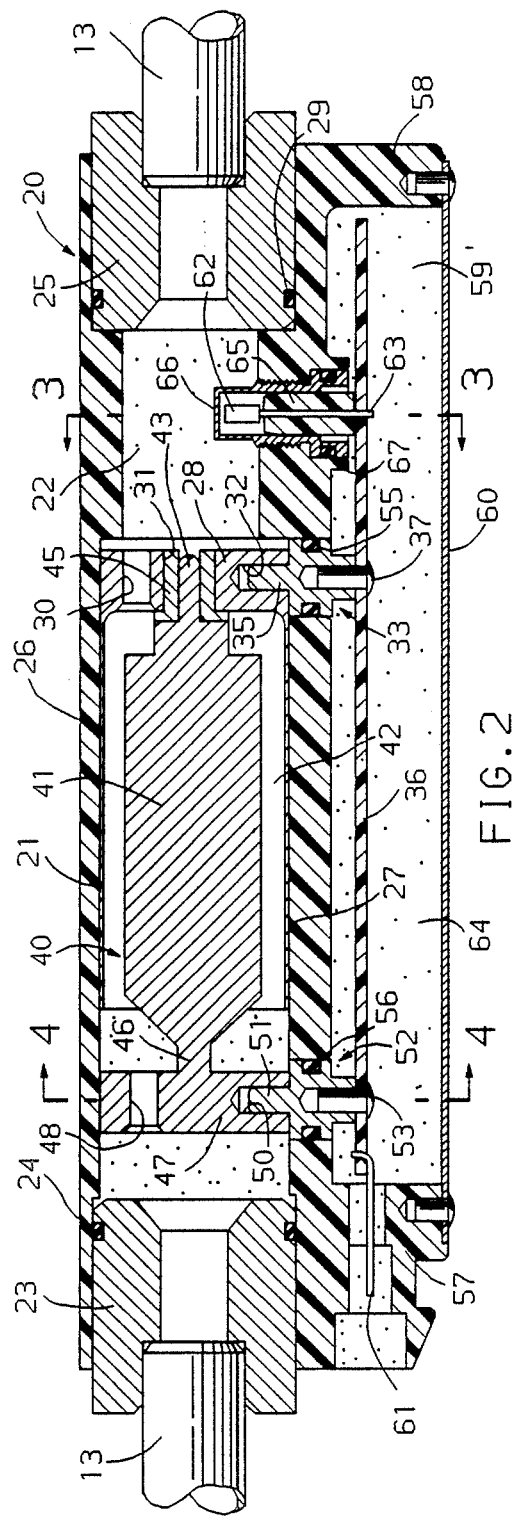
FIG. 2
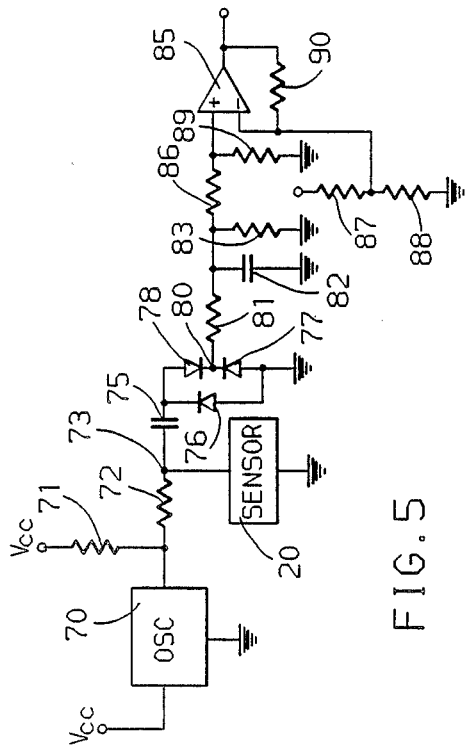
FIG. 6
FIG. 5

COMBUSTION ENGINE WITH MULTI-FUEL CAPABILITY

BACKGROUND OF THE INVENTION

This application is a division of U.S. Ser. No. 07/268,431, filed Nov. 8, 1988, now U.S. Pat. No. 4,915,084 and assigned to the assignee of this application.

This invention relates to combustion engines such as those used to propel motor vehicles, and particularly to such vehicles with multi-fuel capability.

Motor vehicle engines of the prior art have been adapted to operate with a variety of fuels such as gasoline or a constant mixture of gasoline and methanol. However, since each particular fuel or constant fuel mixture has a different energy content and therefore requires a different air/fuel (A/F) mixture for optimal combustion, an engine designed for one fuel or constant fuel mixture did not operate optimally, if it operated at all, with a different fuel or constant fuel mixture.

Therefore the prior art shows systems in which, for some combinations of fuels, the relative concentrations of the fuels in the mixture can be sensed and the A/F ratio provided to the engine controlled in response thereto for optimal combustion. These systems have been designed for mixtures of gasoline and methanol and include optical, microwave and capacitive sensors for methanol concentration.

An optical sensor is shown in U.S. Pat. No. 4,438,749 to Schwippert, issued Mar. 27, 1984, and the paper "Vehicle Operation with Variable Methanol/Gasoline Mixtures", published in May 1984 as part of the VI International Symposium on Alcohol Fuels Technology in Ottawa, Canada. This sensor provides a light tube immersed in the fuel mixture provided to the engine and measures the light transmission of the light tube. The alcohol concentration of the fuel mixture varies the refractive index thereof which, in turn, varies the percentage of light escaping the light tube and thus the light transmissibility thereof. However, aromatics in the in gasoline vary depending on the source of oil from which the gasoline is refined; and the varying aromatics cause a substantial variation in refractive index and thus inaccuracy in the sensor output, since these changes in refractive index do not imply corresponding changes in required A/F ratio. An additional problem with the optical sensor is a clouding of the light path over time, which also affects sensor output.

A capacitive sensor was described in the paper "An On-Board Sensor for Percent Alcohol", published in *IEEE Transactions on Vehicular Technology*, Vol. VT-27, No. 3, Aug., 1978. This sensor provided a capacitor with a fuel mixture of varying dielectric constant determining the capacitance thereof. The capacitance was determined by a circuit similar to that described in U.S. Pat. No. 4,001,676 to Hile et al, issued Jan. 4, 1977. The circuit used a DC charge pumping and threshold detection technique in which the capacitor and a reference capacitor were simultaneously charged and allowed to discharge, with the difference in discharge time indicative of capacitance. Unfortunately, the direct current conductivity of a gasoline/methanol mixture increases significantly with methanol concentration. The circuit of the paper was designed for mixtures up to 30 percent methanol and worked adequately up to that level; but increasing methanol concentration beyond that level leads to failure of accurate sensor response as the fuel conductivity essentially shorts out the capacitor.

A microwave sensor is shown in U.S. Pat. No. 4,453,125 to Kimura et al, issued Jun. 5, 1984. This patent shows a microwave oscillator (1–30 GHz) and receiver connected by a tubular dielectric substrate and strip line. The fuel mixture for the engine flows through the tubular dielectric substrate; and the microwaves attenuate by alcohol dielectric loss, whereby the received microwaves indicate alcohol concentration. The extremely high frequencies of the microwave circuit components allow accurate dielectric constant measurement in spite of the conductivity of fuel mixtures containing high alcohol concentrations. However, the microwave components increase the cost of the sensor and generate a high electromagnetic noise (EMI) level.

SUMMARY OF THE INVENTION

The apparatus of the invention provides for multi-fuel engine operation based on sensing of the dielectric constant of the fuel mixture without the expense and EMI noise level of microwave techniques for fuels such as gasoline with varying aromatics, normal alcohols, TBA, MTBE, and octane, regardless of the number of such fuels in the mixture or their concentrations. It will tolerate a reasonable concentration of water in the fuel mixture and still give accurate results. It allows the sensor to be placed in the fuel line in the heat of a vehicle engine compartment with no ill effects in the sensing so that the sensing apparatus may be placed as closely as possible to the fuel/air induction apparatus for tighter A/F ratio control.

The invention is a combustion engine having a combustion chamber, a fuel tank, a fuel delivery line from the fuel tank to the engine, air/fuel delivery means for pumping a fuel mixture of one or more liquid fuels in any combination from the fuel tank through the fuel delivery line to the combustion chamber in combination with air in a controlled A/F ratio and apparatus for automatically controlling the A/F ratio in response to the dielectric constant of the fuel mixture to provide a desired A/F ratio for combustion of the fuel mixture. The apparatus for controlling the A/F ratio comprises, in combination, a capacitor in the fuel line adapted for fuel flow therethrough so that the fuel pumped to the combustion chamber comprises the dielectric which determines the capacitance thereof, a resistor in series with the capacitor, and an oscillator providing an oscillating voltage of fixed peak-to peak value across the resistor and capacitor. The oscillating voltage has a frequency of oscillation of at least 1 MHz but less than a frequency requiring microwave components. The apparatus further comprises an electric capacitance circuit responsive to a capacitive determined electrical parameter of the capacitor such as the voltage thereacross or phase shift thereof to determine the capacitance thereof and therefore the dielectric constant of the fuel mixture.

With this apparatus, the A/F ratio is adapted for optimal combustion regardless of the constituents and concentrations thereof in the fuel mixture. The apparatus uses a capacitive dielectric constant sensor but is an improvement over prior art in that it uses AC capacitive sensing techniques at a much higher frequency than prior art capacitive fuel sensors to avoid failure at high alcohol concentrations due to high fuel conductivity. The preferred frequency within the claimed frequency range is approximately 10 MHz.

SUMMARY OF THE DRAWINGS

FIG. 2 shows a cutaway view of a capacitive dielectric constant sensor structure for use in the fuel line of the combustion engine of FIG. 1.

FIG. 5 shows an electronic circuit including the capacitive dielectric constant sensor shown in FIGS. 2-4 and additional electronic signal processing apparatus for use in the combustion engine of FIG. 1.

FIG. 6 is a graph of dielectric constant vs. required air/fuel (A/F) ratio for combustion in the combustion engine of FIG. 1 for a variety of fuels.

DESCRIPTION OF THE PREFERRED EMBODIMENT

Figure 1:
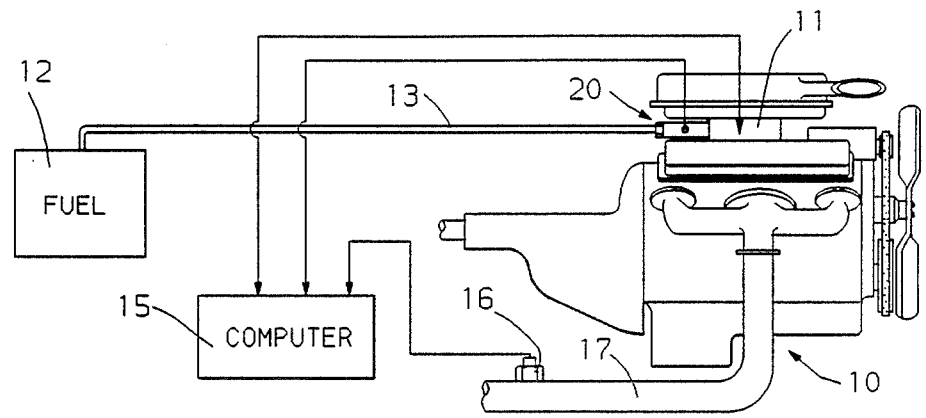
FIG. 1 shows a combustion engine according to the invention.

Referring to FIG. 1, a combustion engine 10 has air/fuel induction apparatus 11 such as a carburetor or fuel injection system, a fuel tank 12 and a fuel line 13 connecting tank 12 to apparatus 11. A fuel pump, which is not shown but may be located within fuel tank 12 or any other convenient location, pumps a fuel mixture from tank 12 to apparatus 11, which provides it along with air in a controlled proportion, to a combustion chamber of engine 10. The proportion of air to fuel or A/F ratio of the fuel mixture provided by apparatus 11 is controlled in response to a signal from a computer 15, which may be a programmed digital computer of the type used in production and well described in the prior art in many variations. It will typically receive input signals from a variety of engine and environmental parameter sensors such as an exhaust gas oxygen sensor 16 in an exhaust line 17 of engine 10 in order to generate the A/F control signal for apparatus 11. However, regardless of the precise configuration of computer 15 and its inputs, it is designed to provide to the combustion chamber of engine 10, at any time, an A/F ratio effective to produce clean and efficient combustion.

Fuel tank 12 contains a fuel mixture which may comprise one or more different fuels in an unknown ratio. One of the fuels may be gasoline, in any of its variants with different aromatics and octane ratings. It may further include any of the normal alcohols such as methanol, ethanol, propanol, butanol, pentanol, octanol, etc. It may include additives such as the alcohol cosolvent TBA, the octane improver MTBE or hydrocarbons such as octane. Each of these fuels has a different energy content and therefore requires a different specific A/F ratio if used by itself; and mixtures of different fuels in different proportions require adjustments of the A/F ratio. In a world of multi-fuel capability, almost any proportion of fuels is possible. For example, a driver with a tank partly full of mostly gasoline with a few additives obtained from a rural service station may top off the tank in an urban station with a fuel comprising mostly methanol. After several such tank fillings at service stations having different fuels or fuel mixtures, the precise proportions of fuels in the tank is unknown even if the precise constitution of the fuel from each service station is known; and accurate determination of required A/F ratio depends on the sensing of a fuel mixture parameter indicative of energy content.

Dielectric constant provides a good parameter for determination of required A/F ratio, as shown in the graph of FIG. 6. The graph plots dielectric constant for a variety of fuels as mentioned above against required A/F ratio and shows that the relationship is essentially linear. Thus, a mixture of any number of these fuels in any concentrations will require an A/F ratio derivable from the dielectric constant of the mixture. Referring again to FIG. 1, a dielectric constant sensor 20 is incorporated in fuel line 13 adjacent apparatus 11. Sensor 20 generates a signal of the dielectric constant of the fuel mixture about to enter the combustion chamber of engine 10 and provides this signal as an additional input to computer 15 for adjustment of the normal A/F signal generated by whatever prior art algorithm is used in computer 15.

Figure 3:
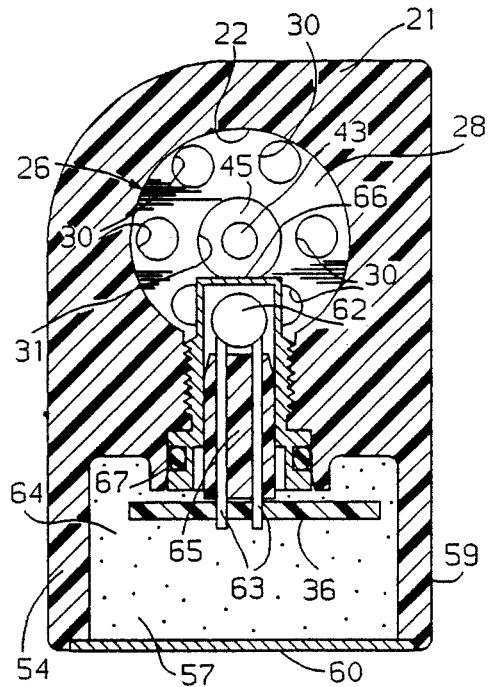
FIGS. 3 and 4 show section views along lines 3—3 and 4—4, respectively, of FIG. 2.
Figure 4:
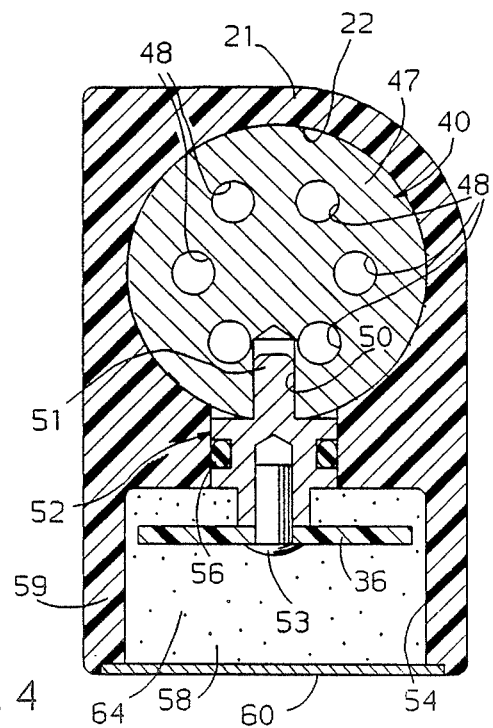

Sensor 20 uses a capacitive determination of the dielectric constant of the fuel mixture. The mechanical structure of sensor 20 is shown in FIGS. 2-4. A casing 21 made of an electrically non-conducting, alcohol resistant material such as nylon defines an internal chamber 22 with openings at each of two ends with stainless steel fittings 23 for insertion of sensor 20 in fuel line 13. Fuel flow direction is through fitting 23, chamber 22 and fitting 25. O-rings 24 and 29 prevent escape of fuel from chamber 22 between casing 21 and fittings 23 and 25, respectively. An outer electrode comprises an outer electrode member 26 of stainless steel having a cylindrical portion 27 fitting just inside casing 21 so that fuel must flow within it. Cylindrical portion 27 of member 26 is open at the left end in FIG. 2 but is attached to a disk portion 28 at the right end. Disk portion 28 includes a plurality of flow openings 30 the total flow area of which is twice the flow area of fuel line 13 so as not to constitute a restriction to fuel flow. Disk portion 28 also has a central opening 31 adapted to support another member to be described and a radially inwardly extending opening 32 which receives a position fixing finger 35 of a electrically conducting support 33 retained in casing 21. Support 33 holds outer electrode member 26 in place axially and prevents its rotation within casing 21 and further provides support for an electrical circuit board 36 just outside casing 21 and fixed to support 33 with a rivet 37. Support 33 further provides electrical connection between outer electrode member 26 and the electronic circuit elements on circuit board 36 to be described in connection with FIG. 5.

An inner electrode member 40 of stainless steel comprises a cylindrical drum portion 41 with an outer surface uniformly spaced from cylindrical portion 27 of outer electrode 26 by an annular gap 42 to form a capacitor with the flowing fuel mixture as the dielectric therebetween. Inner electrode member 40 further comprises, at the right end thereof in FIG. 2, an axially extending shaft 43 retained by an insulating metal bushing 45 within central opening 31 of disk portion 28 of outer electrode member 26. At the left end thereof in FIG. 2, inner electrode member 40 tapers to a small diameter portion 46, to which is attached a disk portion 47 having flow openings 48 similar in size, number and arrangement to flow openings 30 of disk portion 28 and a radially inwardly extending opening 50 receiving a finger 51 of a support 52 in a manner similar to the arrangement of support 33 and disk portion 28. Support 52 further supports circuit board 36 with a rivet 53 and provides electrical connection between inner electrode 40 and the electronic circuit elements on circuit board 36. O-rings 55 and 56 prevent fuel leakage past supports 33 and 52, respectively, through casing 21.

Fuel enters the sensor from fuel line 13 through fitting 23 and flows through openings 48 in disk portion 47 to the annular gap 42 between the cylindrical portions 27 and 41 of outer electrode member 26 and inner electrode member 40, respectively, whereby the dielectric constant of the fuel mixture in annular gap 42 determines the capacitance between the outer and inner electrode members 26 and 40. Supports 33 and 52 hold outer and inner electrode members 26 and 40 in place and communicate them electrically with electronic circuit elements on circuit board 36. Fuel flows from annular gap 42 through openings 30 of disk portion 28 and fitting 25 to fuel line 13 and on to engine 10. Although all openings and gaps within the sensor are of sufficient size to prevent them from presenting a significant restriction to fuel flow, the total volume of fuel contained within chamber 22 is minimized with out of flow volumes eliminated or reduced to prevent extreme flow rate reduction or accumulation of fuel within chamber 22 which might lead to differences in dielectric constant between the fuel mixture in the sensor and that about to enter the combustion chamber of engine 10.

Radial extensions 57 and 58, seen in FIG. 2, extend radially outward from casing 21 and are joined by radial extensions 54 and 59, seen in FIGS. 3 and 4, to define a generally rectangular chamber 64 outside casing 21 around circuit board 36, which chamber is closed for the protection of circuit board 36 from the engine compartment environment by an aluminum cover plate 60. Extension 57 is provided with an axially extending opening to allow access to an electrical connector 61 of circuit board 36. Further mounted in casing 21 and extending into chamber 22 between the capacitor and fitting 25 is a temperature sensor 62, which may be a thermistor or any other type of temperature sensor appropriate for sensing the temperature of fluids. Temperature sensor 62 has leads 63 extending through an insulating plug 65 to connect with electronic elements on circuit board 36, the temperature sensor 62 and insulating plug 65 being retained within a hollow housing 66 made of a good heat conducting material and screwed into casing 21. An O-ring 67 prevents fuel leakage past housing 66. Temperature sensor 62 provides a fuel temperature signal for temperature compensation of the sensed fuel dielectric constant, which signal is also available as an input to computer 15 for other purposes such as canister purge control.

The electronic circuit of the sensor is shown in FIG. 5. An oscillator 70, which may be a Motorola Rasco Plus (T), receives electrical power at a voltage $V_{cc}$ (10 volts) from a regulated DC power supply and generates an output voltage oscillating between ground and 10 volts at a preferred frequency of at least 1 MHz and preferably 10 MHz. The frequency may be higher, as long as it stays below microwave frequencies so that the circuit will operate with lumped parameter circuit elements with no need for more expensive and noisier microwave elements. A pull-up resistor 71 (300 ohms) is connected from the output of oscillator 70 to voltage $V_{cc}$; and the oscillator output voltage is provided across a resistor 72 (100 ohms) and sensor 20 connected in series and defining a junction 73 therebetween. The value of resistor 72 is set to approximately the midpoint of the expected range of impedance for sensor 20 to linearize the output for equivalent sensitivity across the expected range of dielectric constant of the fuel mixture.

Junction 73 is connected through a series DC isolating capacitor 75 (0.01 uF) to a full wave rectifier comprising a diode 76 connected from ground to the side of capacitor 75 opposite sensor 20 and diodes 77 and 78 connected from ground and the same side of capacitor 75 to a junction 80. Because of the high frequency used, diodes 76–78 are MUR110 ultrafast recovery diodes with a 35 nanosecond recovery rate, due to the high frequencies involved. Junction 80 is connected through a low pass filter comprising a series resistor 81 (100 ohms) with a shunt capacitor 82 (0.1 uF) to ground. The output of this low pass filter is a DC voltage indicating the peak to peak value of the voltage across the capacitor of sensor 20. The output of the low pass filter is connected to ground through a resistor 83 and to the non-inverting input of an op-amp 85 (LM2904) through a resistor 86 (1M), the non-inverting input being further connected to ground through a resistor 89 (1M). Resistor 83 may be a 50K potentiometer and is adjusted to produce a full 5 volt voltage span in the output for maximum resolution. Op-amp 85 has an inverting input connected to the junction of resistors 87 (10K) and 88 (1.65K) comprising a voltage divider across $V_{cc}$ and is further connected to its output through a negative feedback resistor 90 (1M). Op-amp 85 and its associated components comprise a subtraction circuit for removing the remnant of DC offset in the output of the low pass filter. The output of op-amp 85 is provided to computer 15. Since it is necessary to compensate the output of sensor 20 for variations in the temperature of the fuel mixture, the output of temperature sensor 62 is also provided to computer 15.

Computer 15 uses the capacitance information from the output of op-amp 85 and the fuel temperature information from temperature sensor 62 to adjust the A/F mixture of the engine to its optimal value for the fuel mixture flowing through sensor 20. For this purpose computer 15 includes a standard read only memory (ROM) containing a 3D lookup table containing compensation factors to be repeatedly looked up with a combination of capacitance and temperature factors: namely, the digitized outputs of op-amp 85 and temperature sensor 62. These compensation factors could be used directly for A/F ratio control; but it is convenient for the ROM to also contain a 2D lookup table for A/F ratio looked up by the compensation factors. The A/F ratio value obtained is used in the normal manner to control the actual A/F ratio of the fuel mixture.

The embodiments of the invention in which an exclusive property or privilege is claimed are defined as follows:

1. A combustion engine having means for providing thereto a fuel mixture of one or more liquid fuels in an unknown combination through a fuel line and means for determining an engine operating control parameter in response to the dielectric constant of the fuel mixture, the last means comprising, in combination:

a capacitor in the fuel line adapted for fuel flow therethrough so that the fuel provided to the combustion engine comprises a dielectric which determines the capacitance thereof;

an impedance in series combination with the capacitor;

an oscillator providing an oscillating voltage to the series combination of the impedance and capacitor, the oscillating voltage having a component with a frequency of oscillation of at least 1 MHz but less than a frequency requiring microwave components; and an electric circuit responsive to a capacitively determined electrical parameter of the capacitor to determine the capacitance thereof and therefore the dielectric constant of the fuel mixture.

2. The combustion engine of claim 1 in which the oscillator provides the oscillating voltage across the series combination of the impedance and the capacitor.

3. The combustion engine of claim 1 in which the capacitively determined electrical parameter to which the electric circuit is responsive is the voltage across the capacitor.

4. The combustion engine of claim 1 in which the impedance is a resistor.

* * * * *